(12) United States Patent
Al-Zahrani et al.

(10) Patent No.: US 8,575,387 B2
(45) Date of Patent: Nov. 5, 2013

(54) METHOD FOR PREPARING CARBOXYLIC ACIDS

(75) Inventors: Saeed Mohammed Al-Zahrani, Riyadh (SA); Horacio Falcon Richeni, Madrid (ES); Ainara Aguadero Garin, Madrid (ES); Jose Antonio Alonso Alonso, Madrid (ES); Jose Miguel Campos Martin, Madrid (ES); Jose Luis Garcia Fierro, Madrid (ES)

(73) Assignee: King Saud University, Riyadh (SA)

( * ) Notice: Subject to any disclaimer, the term of this patent is extended or adjusted under 35 U.S.C. 154(b) by 47 days.

(21) Appl. No.: 13/480,534

(22) Filed: May 25, 2012

(65) Prior Publication Data
US 2013/0144084 A1 Jun. 6, 2013

(30) Foreign Application Priority Data

Dec. 1, 2011 (EP) ..................... 11191555

(51) Int. Cl.
*C07C 51/265* (2006.01)
*C07C 51/10* (2006.01)
*C07C 51/145* (2006.01)

(52) U.S. Cl.
USPC .......................... 562/412; 562/406

(58) Field of Classification Search
None
See application file for complete search history.

(56) References Cited

PUBLICATIONS

Singh et al., Catalysis Communications (2009), 10(15), p. 2004-2007.*
A. Aguadero et al.; An Oxygen-Deficient Perovskite as Selective Catalyst in the Oxidation of Alkyl Benzenes; Angew Chem. Int. Ed. 2011, 50, 6557-6561.

* cited by examiner

*Primary Examiner* — Brian J Davis
(74) *Attorney, Agent, or Firm* — Renner, Otto, Boisselle & Sklar, LLP

(57) ABSTRACT

The present invention relates to a method for preparing carboxylic acids comprising the step of contacting an aromatic hydrocarbon comprising at least one group including an α C-atom that is oxidizable to a carboxylic group in liquid phase with an oxygen containing gas in the presence of a heterogeneous catalyst with perovskite structure $ABO_3$ with A being selected from at least one element of groups 1 to 3 of the Periodic Table, lanthanides or actinides, and B being selected from at least one element of the groups 4 to 15 of the periodic table or an oxygen-defective derivative of that catalyst having the formula $ABO_{3-\delta}$ with $0<\delta<1$.

22 Claims, No Drawings

METHOD FOR PREPARING CARBOXYLIC ACIDS

The present invention relates to a method for preparing carboxylic acids.

Carboxylic acids are important compounds in the field of chemistry, both for direct industrial use or as intermediate product for further conversion. For example, organic acids derived from alkyl aromatics are a starting material to produce polyester fiber, polyester film, bottles, etc. The polyester fibers are used in textile goods and for industrial use as well, such as tire code, and the polyester film being coated with adhesive or emulsion is useful for wrapping tape, photographic film, and recording tape.

In commercial practice, aromatic carboxylic acids are commonly produced by converting methyl-substituted benzene and naphthalene feedstocks a liquid-phase oxidation in an aqueous acetic acid solvent. The positions of the methyl substituents of the starting material correspond to the positions of the carboxyl groups in the desired aromatic carboxylic acid product. Oxidation is conducted by contacting the feedstock with air or another source of oxygen, which is normally gaseous, in the presence of a catalyst comprising cobalt and manganese promoted with a source of reactive bromine. The oxidation is exothermic. The aromatic carboxylic acid oxidation product, and by-products, such as methanol, methyl acetate, methyl bromide, carbon monoxide and carbon dioxide, are commonly formed dissolved or as solid suspended in the liquid phase reaction mixture and are recovered by crystallization and solid-liquid separation techniques.

A suitable oxidation catalyst composition includes a cobalt compound and a manganese compound, usually in combination with a promoter such as a bromine compound, see for example U.S. Pat. Nos. 2,833,816, 2,962,361, 3,089,906, 3,970,696, 4,159,307, 4,314,073, 4,327,226, 5,679,847, 5,756,833, 2002/0193630, 2002/0183546, 2010/0056750, JP 1997278709, GB 1 389 478, WO2006/096311, WO2008/097393 and WO2009/038045.

Difficulties in the manufacture of aromatic carboxylic acids arise from the use of bromine-promoted oxidation catalysts. Bromine sources used with a catalyst and reaction products thereof formed during oxidation are corrosive. Consequently, process equipment, such as oxidation reactors and off-gas treatment equipment, is normally constructed from titanium or other expensive, corrosion-resistant metals or alloys. In addition, process off-gas treatments to avoid atmospheric emissions of volatile bromine compounds, such as thermal or catalytic oxidation to convert organic bromine compounds to carbon oxides and molecular bromine with reduction of the latter to anionic bromine using sodium formate add complexity and cost to manufacturing processes, see, for example U.S. Pat. No. 3,012,038. These corrosion problems can be reduced using molten salts, see US 2009/0326265 and WO2008/074497 A1.

The key challenge for the commercial development and practical use of homogeneous catalysts is the separation of product from the catalytic medium. This process is often complicated and usually accomplished by means of complex work-up procedures. Attempts to improve catalyst recovery and recycling include the use of biphasic systems or the immobilization of catalysts on supports.

Some attempts have been made to use heterogeneous catalysts. U.S. Pat. No. 3,865,870 proposes the use noble metal-catalysts for oxidizing methylated benzenes, but conversion and selectivity to aromatic carboxylic acids are low and carbon oxides generation is high. US 2010/0145094 A1 and US 2009/0118536 A1 propose the use of modified palladium heterogeneous catalysts for the alkyl aromatics selected oxidation to aromatic carboxylic acids. But the use of noble metals makes the catalysts expensive.

It is therefore an object of the present invention to provide a method for preparing carboxylic acids which overcomes the difficulties of the prior art. Especially, a method shall be provided wherein a heterogeneous catalyst is utilized which can be easily recovered from the reaction medium is inexpensive and results in the production of carboxylic acids with high conversion and selectivity.

This object is achieved by a method for preparing carboxylic acids comprising the step of contacting an aromatic hydrocarbon comprising at least one group including an α C-atom that is oxidizable to a carboxylic group in liquid phase with an oxygen containing gas in the presence of a heterogeneous catalyst with perovskite structure $ABO_3$ with A being selected from at least one element of groups 1 to 3 of the Periodic Table, lanthanides or actinides, and B being selected from at least one element of the groups 4 to 15 of the periodic table or an oxygen-defective derivative of that catalyst having the formula $ABO_{3-\delta}$ with $0<\delta<1$.

It is a core feature of the present invention that a heterogeneous catalyst based on perovskite structure $ABO_3$ is utilized in the method for preparing carboxylic acids.

A perovskite is a material with the same type of crystal structure as calcium titanium oxide ($CaTiO_3$), known as the perovskite structure. In perovskite-type oxides represented by $ABO_3$, the B-site cation is surrounded three octahedral by oxygen and the A-site cation is located in the cavity made between these octahedral. An interesting characteristic of this structural type is its chemical flexibility, accepting a wide variety of cations at the A or B sublattices, thereby chancing the covalency of the B—O bonds. Moreover, partial substitution at the A site can strongly affect the catalytic activity through the stabilisation of unusual oxidation states of the B component and the simultaneous formation of structural defects. An important feature of perovskite-type oxides is that they are able to accept and accommodate large amounts of oxygen vacancies, concomitant with changes in the oxidation states of the transition metals located at B sites. The structural defects are responsible not only for part of the catalytic activity, but also for the mobility of oxygen atoms within the crystal lattice, see Tejuca, L. G. et al.; Adv. Cat al. 1989, 36, 237, and Peña, M. A.; et al., Chem. Rev. 2001, 101, 1981.

The preparation of these compounds is widely known, see the references given above and references therein. The perovskite-type heterogeneous catalyst used in the method of the present invention shall comprise compounds having more than one A and B element, such as the compound having the formula of $A_{1-x}A'_xB_{1-x}B'_xO_3$ with $0<x<1$, and also oxygen-defective perovskite structures, such as $ABO_{3-\delta}$ with $0<\delta<1$.

Preferably B is selected from at least one of Ti, V, Cr, Mn, Fe, Co, Ni, and Cu.

More preferably the amount of a heterogeneous catalyst is in the range of 0.0001 to 20 weight percent, preferably from 0.001 to 5 weight percent, based on the amount of the aromatic hydrocarbon.

The term "aromatic compound" shall also comprise heteroaromatic compounds.

Suitable alkyl substituted aromatic feed materials for the oxidation generally comprise an aromatic hydrocarbon substituted at one or more positions, normally corresponding to positions of the carboxylic acid groups of the aromatic carboxylic acid being prepared, with at least one group that includes an α C-atom that is oxidizable to a carboxylic acid group. The oxidizable substituent or substituents can be alkyl groups, such as a methyl, ethyl or isopropyl, or groups already containing oxygen, such as formyl, acyl or hydroxyalkyl groups. Substituents can be the same or different. The aromatic ring can be a benzene nucleus or bi- or polycyclic, such as a naphthalene nucleus. The number of oxidizable substituents of the aromatic compound can equal the number of sites available on the aromatic ring, but is generally less, preferably 1 or 2, and most preferably 2. Examples of useful feed compounds, which can be used alone or in combinations, include toluene, ethylbenzene and other alkyl-substituted benzenes, o-xylene, p-xylene, m-xylene, tolualdehydes, toluic acids, alkyl benzyl alcohols, 1-formyl-4-methylbenzene, 1-hydroxymethyl-4-methylbenzene, methylacetophenone, 1,2,4-trimethylbenzene, 1-formyl-2,4-dimethylbenzene, 1,2,4,5-tetramethyl-benzene, alkyl-, formyl-, acyl-, and hydroxylmethyl-substituted naphthalenes, such as 2,6-dimethylnaphthalene, 2,6-diethylnaphthalene, 2,7-dimethylnaphthalene, 2,7-diethylnaphthalene, 2-formyl-6-methyl-naphthalene, 2-acyl-6-methyl-naphthalene, 2-methyl-6-ethylnaphthalene and partially oxidized derivatives thereof.

Any oxygen containing gas can be applied, like molecular oxygen, air or any other gas mixture comprising oxygen, e.g. carbon dioxide. In a preferred way of performing the method according to the invention the oxygen containing gas comprises 4-50 volume percent of carbon dioxide, preferably 10-25 volume percent. This further reduces reaction time and side-reactions. The ratio of total amount of oxygen to the substituted aromatic compound is depending on the number of substituents to be oxidized. Preferably, oxygen is used in excess; for example the molar ratio of oxygen to aromatic compound is from 3 to 500, more preferably from 5 to 100. The method of the present invention is conducted in a liquid phase. The method can be conducted in the presence or absence of solvents.

When a solvent is used, water, (mono)carboxylic acid and their mixtures are preferred, but other suitable solvents or liquid media can be used. Preferred solvents for aromatic feed materials in the liquid phase reaction comprise low molecular weight monocarboxylic acids and preferably a $C_1$-$C_{14}$ monocarboxylic acid, for example acetic acid, propionic acid, butyric acid, valeric acid and benzoic acid. Acetic acid is a preferred monocarboxylic acid.

In a preferred embodiment, a promoter may be added to the inventive process. As promoter an imide compound is added. Preferred imide compounds are cyclic N-hydroxyimides. Examples of the cyclic N-hydroxyimide in the present invention include: N-hydroxysuccinimide, N-hydroxyphthalimide, N-hydroxymaleimide, N-hydroxynaftenimide, N,N'-dihydroxypyromellitimide, and other N-hydroxyimide compounds derived from aliphatic dicarboxylic anhydrides, alicyclic polycarboxylic anhydrides or aromatic polycarboxylic anhydrides, of which those derived from aliphatic dicarboxylic anhydrides or aromatic polycarboxylic anhydrides are especially preferred; and compounds obtained by introducing a protecting group into the hydroxyl group of these N-hydroxyimide compounds. The applied reaction conditions, temperature and pressure, in the reaction zone are such that a liquid is maintained, and that the desired reaction occurs to obtain a desired conversion, yet not such that substantial evaporation or undesirable side reactions occur.

Preferably the promoter is present in an amount of about 0.000001 to about 0.1 mole per mole of aromatic hydrocarbon.

In one embodiment the method is carried out at a temperature in the range of 60-300° C., preferably 90-200° C.

Even preferred the method is carried out at a pressure at a range of 0.1-10 MPa, preferably 0.1-2.0 MPa.

In one further embodiment the method is carried out in a reactor having a resin time of about 60-120 minutes.

It is preferred that the heterogeneous catalyst is pre-treated by heating thereof in the presence of an inert gas or in the presence of a gas containing a reducing agent, such as hydrogen, carbon monoxide, or hydrazine. Preferred inert gases are nitrogen, argon or a carbon dioxide. Preferably, pre-treatment is conducted at a temperature range between 100 and 800° C., more preferably between 300 and 700° C.

Finally, the method is carried out, as A is selected from at least one element of group 2 of the periodic table, lanthanum or lanthanoid elements, preferably Ca, Sr, Ba, La, Ce, Pr, Nd and Sm.

The reaction zone in the method according to the invention can include one or more reactors as known to any skilled person, for example a stirred tank reactor that may be operated in continuous or batch-wise way.

The method according to the invention may further comprise additional steps to isolate and purify the aromatic acid as obtained by the method as described above. Such processing steps are well know to the skilled person and have been described in the general literature.

In one preferred embodiment, separation of the heterogeneous catalyst can be achieved by applying a magnetic field if the perovskite is magnetic as such. This is especially true if Co or Fe have been chosen in the perovskite structure.

Surprisingly it was found that the inventive method produces carboxylic acids using a heterogeneous catalyst which can be easily recovered from the reaction media. The hydrogeneous catalyst is inexpensive and produces the carboxylic acid with high conversion and selectivity.

Additional features and advantages of the inventive method shall be further illustrated on the basis of the following examples.

EXAMPLE 1

Synthesis of $La_{0.5}Sr_{0.5}Mn_{0.5}Co_{0.5}O_3$ Perovskite

Equimolecular amounts of commercial $La_2O_3$, $Sr(NO_3)_2$, $MnCO_3$ and $Co(NO_3)_2 \cdot 6H_2O$ were dissolved in an aqueous solution of citric acid under stirring. The solution was slowly evaporated, leading to an organic resin which was dried at 120° C. and slowly decomposed at temperatures up to 800° C. The sample was then calcined at 1150° C. for 12 h in air obtaining a black, well-crystallized powder corresponding to an oxygen-stoichiometric $La_{0.5}Sr_{0.5}Mn_{0.5}Co_{0.5}O_3$ perovskite.

EXAMPLE 2

Synthesis of Oxygen-Defective $La_{0.5}Sr_{0.5}Mn_{0.5}Co_{0.5}O_3$ Perovskite

The material obtained in Example 1 was treated at 500° C. for 6 h in a 5% $H_2$/95% $N_2$ flow. This treatment led to the formation of the oxygen-defective $La_{0.5}Sr_{0.5}Mn_{0.5}Co_{0.5}O_{3-\delta}$ perovskite oxide with $\delta=0.02$.

EXAMPLE 3

Synthesis of $SrCo_{0.9}Sb_{0.1}O_3$ Perovskite 1 mol of $Sr(NO_3)_2$, 0.9 mol of $Co(NO_3)_2 \cdot 6H_2O$ and 0.1 mol of $Sb_2O_3$ were dissolved in an aqueous solution of citric acid under stirring, adding some droplets of nitric acid. The solution was slowly evaporated, leading to an organic resin which was dried at 120° C. and slowly decomposed at temperatures up to 800° C. The sample was then calcined at 1150° C. for 12 h in air obtaining a black, well-crystallized powder corresponding to $SrCo_{0.9}Sb_{0.1}O_3$ perovskite.

EXAMPLE 4

Synthesis of $LaSrCoTiO_6$ Perovskite

Equimolecular amounts of commercial $La_2O_3$, $Sr(NO_3)_2$, $Co(NO_3)_2 \cdot 6H_2O$ and $TiC_{10}H_{14}O_5$ were dissolved in an aqueous solution of citric acid under stirring adding some droplets of nitric acid. The solution was slowly evaporated, leading to an organic resin which was dried at 120° C. and slowly decomposed at temperatures up to 800° C. The sample was then calcined at 1150° C. for 12 h in air obtaining a black, well-crystallized powder corresponding to $LaSrCoTiO_6$ perovskite.

EXAMPLE COMPARATIVE 1

Following the procedure described in the US Pat. Publn. No. US 2004/0024248. In a 100 mL stainless steel stirred reactor 1.46 g of p-xylene; 21 g of acetic acid, 0.0166 g of cobalt(II) acetate, 0.0115 g of manganese(II) acetate and 0.435 g of N-hydroxyphthalimide were mixed. The reactor was heated to 90° C., and the pressure was increased to 20 bar with oxygen. The stirring was started up (1500 rpm) to initiate the reaction. After the reaction time of 3 h, the p-xylene conversion was 100% and the selectivity to terephthalic acid was 58% and to p-toluic acid 37%.

EXAMPLE 5

In a 100 mL stainless steel stirred reactor 1.46 g of p-xylene; 21 g of acetic acid, 0.005 g of solid prepared in Example 1 and 0.435 g of N-hydroxyphthalimide were mixed. The reactor was heated to 90° C., and the pressure was increased to 20 bar with oxygen. The stirring was started up (1500 rpm) to initiate the reaction. After a reaction time of 3 h, the p-xylene conversion was 100% and the selectivity to terephthalic acid was 26% and to p-toluic acid 70%.

EXAMPLE 6

In a 100 mL stainless steel stirred reactor 1.46 g of p-xylene; 21 g of acetic acid, 0.005 g of solid prepared in Example 2 and 0.435 g of N-hydroxyphthalimide were mixed. The reactor was heated to 90° C., and the pressure was increased to 20 bar with oxygen. The stirring was started up (1500 rpm) to initiate the reaction. After a reaction time of 5 h, the p-xylene conversion was 100% and the selectivity to terephthalic acid was 97% and to p-toluic acid 3%.

EXAMPLE COMPARATIVE 2

In a 100 mL stainless steel stirred reactor 1.46 g of toluene; 21 g of acetic acid, 0.0166 g of cobalt(II) acetate, 0.0115 g of manganese(II) acetate and 0.435 g of N-hydroxyphthalimide were mixed. The reactor was heated to 100° C., and the pressure was increased to 50 bar with air. The stirring was started up (1500 rpm) to initiate the reaction. After a reaction time of 3 h, the toluene conversion was 98% and the selectivity to benzoic acid was 99% and 1% to benzaldehyde.

EXAMPLE 7

In a 100 ml stainless steel stirred reactor 1.46 g of toluene; 21 g of acetic acid, 0.005 g of solid prepared in Example 2 and 0.435 g of N-hydroxyphthalimide were mixed. The reactor was heated to 100° C., and the pressure was increased to 20 bar with oxygen. The stirring was started up (1500 rpm) to initiate the reaction. After a reaction time of 3 h, the toluene conversion was 100% and the selectivity to benzoic acid was 99.4% and 0.6% to benzaldehyde.

EXAMPLE 8

In a 100 ml stainless steel stirred reactor 1.46 g of toluene; 21 g of acetic acid, 0.005 g of solid prepared in Example 3 and 0.435 g of N-hydroxyphthalimide were mixed. The reactor was heated to 100° C., and the pressure was increased to 20 bar with oxygen. The stirring was started up (1500 rpm) to initiate the reaction. After a reaction time of 3 h, the toluene conversion was 90% and the selectivity to benzoic acid was 98% and 2% to benzaldehyde.

EXAMPLE 9

In a 100 ml stainless steel stirred reactor 1.46 g of toluene; 21 g of acetic acid, 0.005 g of solid prepared in Example 4 and 0.435 g of N-hydroxyphthalimide were mixed. The reactor was heated to 100° C., and the pressure was increased to 20 bar with oxygen. The stirring was started up (1500 rpm) to initiate the reaction. After a reaction time of 3 h, the toluene conversion was 100% and the selectivity to benzoic acid was 98% and 2% to benzaldehyde.

EXAMPLE COMPARATIVE 3

In a 100 mL stainless steel stirred reactor 1.46 g of ethylbenzene; 21 g of acetic acid, 0.0166 g of cobalt(II) acetate, 0.0115 g of manganese(II) acetate and 0.435 g of N-hydroxyphthalimide were mixed. The reactor was heated to 100° C., and the pressure was increased to 20 bar with oxygen. The stirring was started up (1500 rpm) to initiate the reaction. After a reaction time of 3 h, the ethylbenzene conversion was 98% and the selectivity to benzoic acid was 7% and 93% to acetophenone.

EXAMPLE 10

In a 100 mL stainless steel stirred reactor 1.46 g of ethylbenzene; 21 g of acetic acid, 0.005 g of solid prepared in Example 2 and 0.435 g of N-hydroxyphthalimide were mixed. The reactor was heated to 100° C., and the pressure was increased to 20 bar with oxygen. The stirring was started up (1500 rpm) to initiate the reaction. After a reaction time of 3 h, the ethylbenzene conversion was 100% and the selectivity to benzoic acid was 63% and 37% to acetophenone.

The features disclosed in the foregoing description and in the claims may, both separately and in any combination thereof, be material for realising the invention in diverse forms thereof.

The invention claimed is:

1. Method for preparing carboxylic acids comprising the step of contacting an aromatic hydrocarbon comprising at least one group including an α C-atom that is oxidizable to a carboxylic group in liquid phase with an oxygen containing gas in the presence of a heterogeneous catalyst with perovskite structure $ABO_3$ with A being selected from at least one element of groups 1 to 3 of the Periodic Table, lanthanides or actinides, and B being selected from at least one element of the groups 4 to 15 of the periodic table or an oxygen-defective derivative of that catalyst having the formula $ABO_{3-\delta}$ with $0 < \delta < 1$.

2. Method according to claim 1, wherein the aromatic hydrocarbon is an alkyl substituted hydrocarbon.

3. Method according to claim 1, wherein the oxygen containing gas is selected from the group consisting of molecular oxygen, air, carbon dioxide or mixtures thereof.

4. Method according to claim 1, wherein B is selected from at least one of Ti, V, Cr, Mn, Fe, Co, Ni, and Cu.

5. Method according to claim 1, wherein the method is carried out in the presence of a solvent.

6. Method according to claim 1, wherein the amount of the heterogeneous catalyst is in the range of 0.0001 to 20 weight percent, based on the amount of the aromatic hydrocarbon.

7. Method according to claim 1, wherein an imide compound is added as promoter.

8. Method according to claim 7, wherein the promoter is present in an amount of about 0.000001 to about 0.1 mole per mole of aromatic hydrocarbon.

9. Method according to claim 1, wherein the method is carried out at a temperature in the range of 60-300° C.

10. Method according to claim 1, wherein the method is carried out at a pressure at a range of 0.1-10 MPa.

11. Method according to claim 1, wherein the method is carried out in a reactor having a residence time of about 60-120 minutes.

12. Method according to claim 1, wherein the heterogeneous catalyst is pre-treated by heating thereof in the presence of an inert gas or in the presence of a gas containing a reducing agent.

13. Method according to claim 1, wherein A is selected from at least one element of group 2 of the periodic table, lanthanum or lanthanoid elements.

14. Method according to claim 5, wherein the solvent is selected from the group consisting of water, carboxylic acid and mixtures thereof.

15. Method according to claim 6, wherein the amount of the heterogeneous catalyst is in the range from 0.001 to 5 weight percent, based on the amount of the aromatic hydrocarbon.

16. Method according to claim 9, wherein the method is carried out at a temperature in the range of 90-200° C.

17. Method according to claim 10, wherein the method is carried out at a pressure at a range of 0.1-2.0 MPa.

18. Method according to claim 12, wherein the gas containing a reducing agent comprises hydrogen, carbon monoxide, or hydrazine.

19. Method according to claim 12, wherein the pre-treatment is conducted at a temperature range between 100 and 800° C.

20. Method according to claim 12, wherein the pre-treatment is conducted at a temperature range between 300 and 700° C.

21. Method according to claim 13, wherein A is at least one element of Ca, Sr, Ba, La, Ce, Pr, Nd and Sm.

22. Method according to claim 2, wherein the aromatic hydrocarbon is selected from the group consisting of toluene, ethyl benzene, p-xylene, o-xylene and m-xylene.

* * * * *